United States Patent [19]

Brisson et al.

[11] Patent Number: 4,644,958
[45] Date of Patent: Feb. 24, 1987

[54] INHALATION THERAPY APPARATUS ADAPTER

[75] Inventors: Alfred G. Brisson, Schaumburg; Christopher Nowacki, Arlington Heights, both of Ill.

[73] Assignee: Trutek Research, Inc., Lake Zurich, Ill.

[21] Appl. No.: 838,188

[22] Filed: Mar. 7, 1986

Related U.S. Application Data

[63] Continuation of Ser. No. 593,412, Mar. 26, 1984, abandoned.

[51] Int. Cl.[4] .................................................. A61B 5/08
[52] U.S. Cl. .................................... 128/725; 73/861.52
[58] Field of Search .................... 128/725, 726, 204.23; 73/861.52, 861.63, 861.66

[56] References Cited

U.S. PATENT DOCUMENTS

| | | | |
|---|---|---|---|
| 3,555,555 | 1/1971 | Lambert | 128/726 |
| 3,605,729 | 9/1971 | Liu et al. | 128/726 |
| 3,680,378 | 8/1972 | Aurilio et al. | 128/726 |
| 3,922,525 | 11/1975 | Kozak et al. | 128/725 |
| 4,425,805 | 1/1984 | Ogura et al. | 128/725 |
| 4,444,201 | 4/1985 | Itoh | 128/725 |

*Primary Examiner*—Henry J. Recla
*Attorney, Agent, or Firm*—Trexler, Bushnell & Wolters, Ltd.

[57] ABSTRACT

A throw-away plastic mouthpiece of low cost and producing a pressure differential upon inhalation is substituted for the rotary turbine and electronics mouthpiece of a known Spirocare respiratory therapy apparatus. The pressure differential is converted to a voltage by a pressure-to-voltage transducer, which voltage is highly amplified by a drift free amplifier. The amplifield voltage is applied to an adapter electronic circuit which produces a succession of negative going pairs of pulses exactly simulating the pulses from the Spirocare mouthpiece. The amplifier and adapter circuitry fit within the cavity provided in the Spirocare apparatus for storage of the mouthpiece, thereby adapting the Spirocare apparatus for use with an inexpensive, throw-away mouthpiece which need not be sterilized, and which is cheap to replace in the event of breakage.

12 Claims, 5 Drawing Figures

INHALATION THERAPY APPARATUS ADAPTER

This application is a continuation, of application Ser. No. 593,412, filed Mar. 26, 1984 now abandoned.

RELATED APPLICATIONS

The present invention is related to three pending applications earlier filed in our names and assigned to the same assignee as the present application, namely, Trutek Research, Inc., of Arlington Heights, Illinois, said applications comprising: Ser. No. 394,403, filed July 1, 1982 now U.S. Pat. No. 4,456,016 for INHALATION VALVE; Ser. No. 415,735, filed Sept. 7, 1982 for INHALATION TRANSDUCER CIRCUIT; and Ser. No. 464,219, filed Feb. 7, 1983 for INHALATION THERAPY APPARATUS now U.S. Pat. No. 4,495,944.

BACKGROUND OF THE INVENTION

In our aforesaid application, Ser. No. 464,219 now U.S. Pat. No. 4,495,944 we have disclosed and claimed an apparatus adapted to provide visual goals and indicia of attainment in respiratory therapy. In accordance with that application a goal is preset by or for the patient which the patient should attain. A visual display is made of the goal as set, and when the patient inhales a visual display is made of the level of attainment, immediately adjacent to the visual display goal. Since the patient can see the side-by-side comparison, there is a greater incentive for him to try harder, thereby to inhale more deeply then he otherwise might do. The electronic control for the apparatus provides a visual recordation of the goals attempted and number of times the goal has been achieved.

In accordance with that application there is provided a throw-away mouthpiece of molded plastic construction and of low cost. This mouthpiece is specifically disclosed and claimed in our aforesaid application Ser. No. 394,403 now U.S. Pat. No. 4,456,016. A diaphragm or flap valve is provided in the mouthpiece. Upon inhalation the valve closes and air is directed through a passageway having a restriction therein, thereby providing a pressure drop. Upon exhalation the valve opens, and the air simple passes through with no pressure drop.

The pneumatic pressure differential is converted into an electric signal as disclosed in our application Ser. No. 415,735 for use in the Inhalation Therapy Apparatus of our application Ser. No. 464,219 now U.S. Pat. No. 4,495,944.

There is in the marketplace another inhalation therapy apparatus providing a goal display and a display of attainment. This is the "Spirocare" apparatus sold by Marion Laboratories, Inc. The Spirocare apparatus ulitizes a mouthpiece containing a small turbine rotor. The turbine rotor is provided with holes for cooperation with a light source and a light sensing element, and an electrical signal is developed, commensurate with the speed of rotation of the turbine rotor, and hence with the volume of air inhaled. The mouthpiece includes an electronic circuit board as well as the turbine rotor. A portion of the mouthpiece including the turbine rotor is replaceable, but this portion is somewhat expensive to produce due, for example, to the need for precision bearings for the rotor. The portion of the mouthpiece including the electronics is very expensive, and is reused from one patient to another, thus presenting some danger of cross-contamination.

For sanitary reasons hospitals generally have hard floors, and it has been found that if the Spirocare mouthpiece is dropped on such a floor it is likely to cause breakage of part of the plastic housing, or damage to the electronics. Repairs are expensive.

There is a large number of Spirocare apparatus in the field, and many problems would be solved if it were possible to use a throw-away mouthpiece that would be totally discarded after use by one patient, with a new mouthpiece being used for each patient. This has heretofore been impossible.

OBJECTS AND SUMMARY OF THE PRESENT INVENTION

It is an object of the present invention to provide a throw-away mouthpiece and electronic adapter for the aforesaid Spirocare apparatus.

In attaining this object we provide a throw-away mouthpiece as disclosed and claimed in our aforesaid application Ser. No. 394,403, now U.S. Pat. No. 4,456,016 and an electronic circuit to convert the pressure differential so developed into an electrical signal, said circuit in part being the same as that in our aforesaid application Ser. No. 415,735. In addition, we provide an electrical circuit for converting the aforesaid electrical signal into two series of pulses identical to those provided by the Spirocare mouthpiece. The electronic circuits are mounted in a housing which fits within the mouthpiece storage cavity of the Spirocare apparatus and plugs into the electrical circuitry of the Spirocare apparatus.

DRAWING DESCRIPTION

The present invention will best be understood with reference to the following specification when taken in connection with the accompanying drawings wherein:

FIG. 1 comprises a perspective view of the Spirocare apparatus with the apparatus and circuitry of the present invention for utilizing a throw-away mouthpiece;

DETAILED DISCLOSURE OF THE ILLUSTRATED EMBODIMENT

Figure 1:
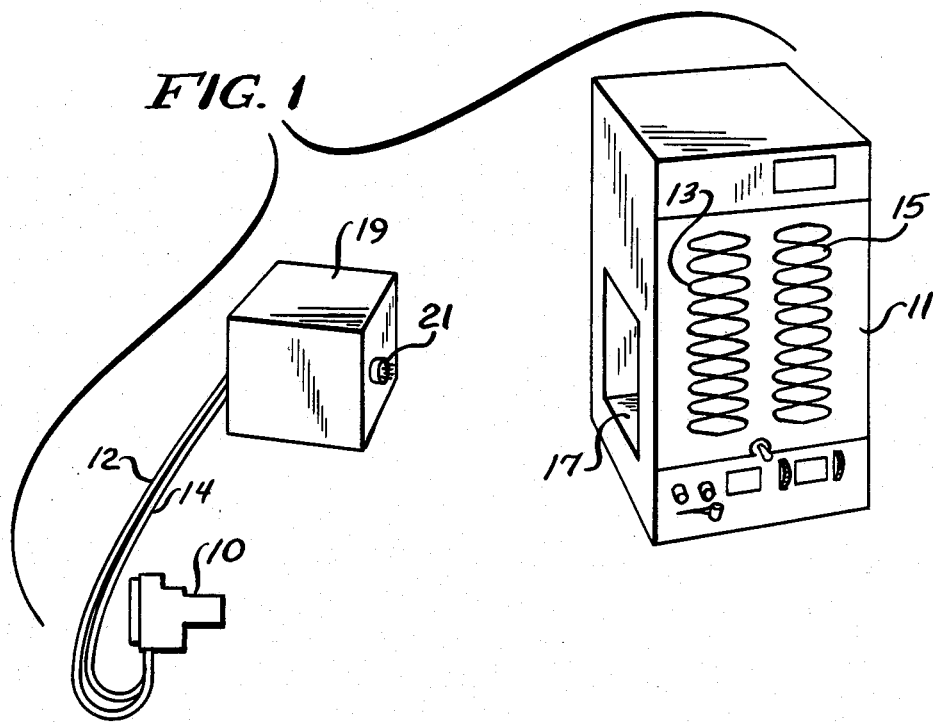
Figure 2:
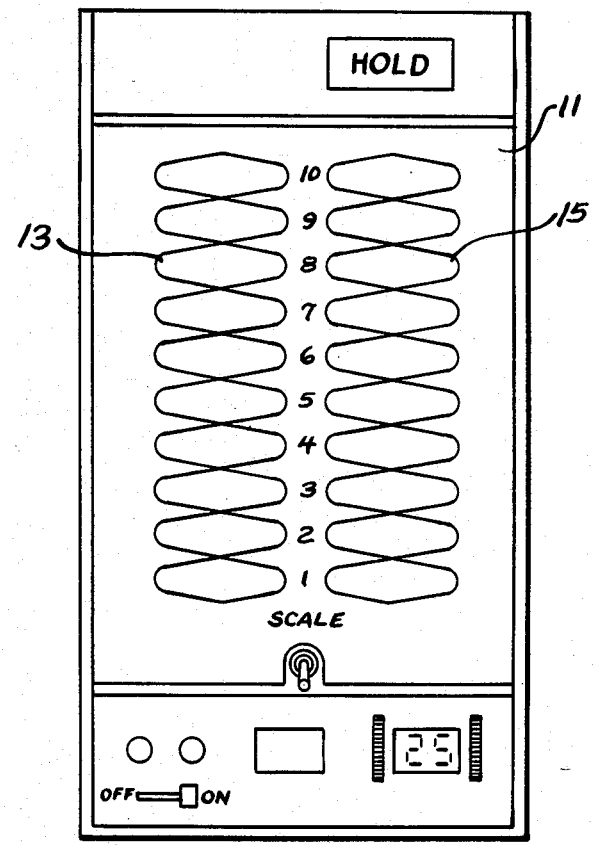
FIG. 2 is a front view of the Spirocare apparatus.

Turning now in greater particularity to the drawings, and first to FIGS. 1 and 2, there will be seen the known Spirocare apparatus 11 having various controls on the face thereof, and two columns 13 and 15 of illuminable indicia. Indicia in one column are illuminated in advance to indicate the desirable goal of inhalation, and the second column lights up as the patient inhales and tries to light the column to the same height as the illumination of the preset column. The Spirocare apparatus includes a housing, and has on the left side thereof a cavity 17 for storing the mouthpiece and connecting wire. A four pin socket (not shown) is provided on the inner most wall for receipt of a plug connecting with the mouthpiece. There is preferably a door (not shown) covering the cavity 17.

In accordance with the present invention electronic circuits disclosed hereinafter are mounted in a rectangular housing 19 of a suitable size to fit within the cavity 17. The housing has on its right wall a four pin plug 21 for cooperation with the socket in the cavity. A throw-away mouthpiece 10 is connected by pneumatic tubing 12 and 14 to the housing 19, and specifically the electronic circuits therein. This mouthpiece preferably is identical with that shown and described in our aforesaid application Ser. No. 394,403, filed July 1, 1982 now U.S. Pat. No. 4,456,016.

Figure 3:
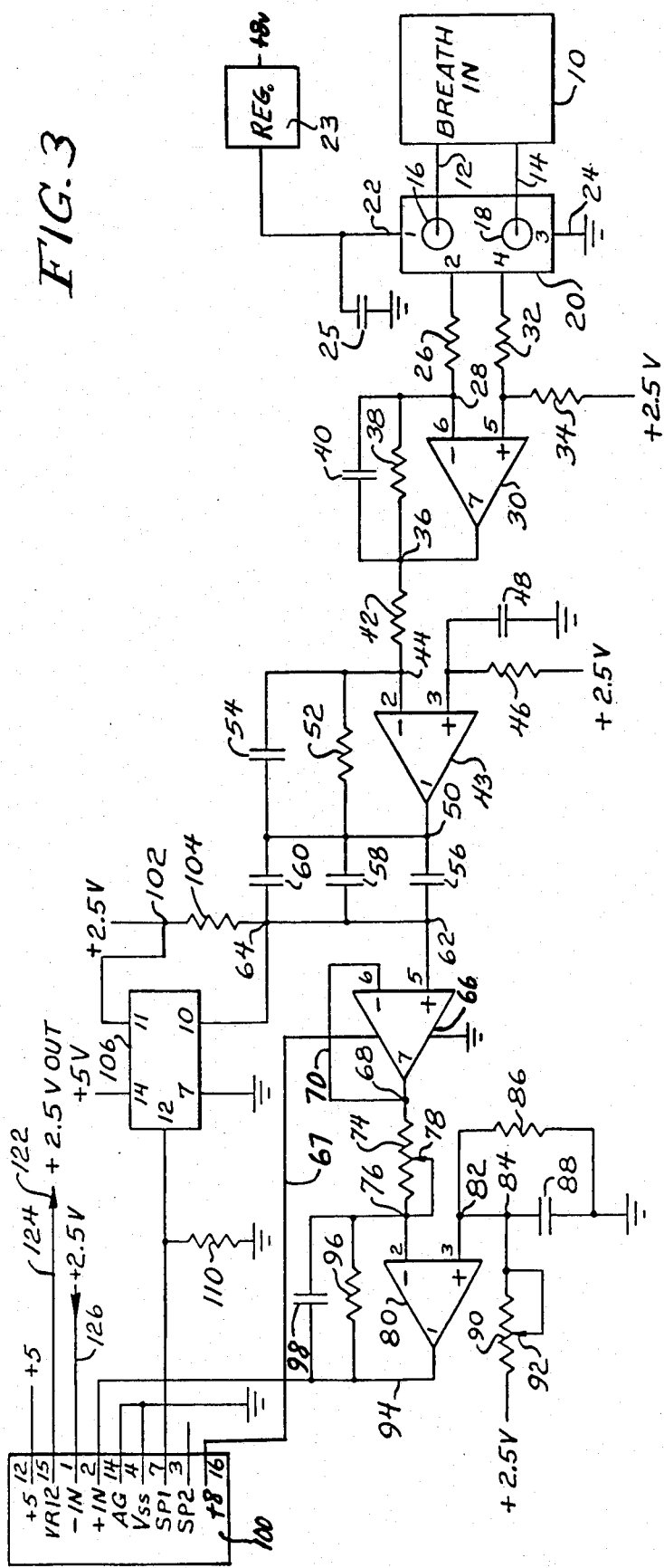
FIG. 3 is an electronic circuit diagram of the transducer amplifier forming a part of the present invention.

Attention now should be directed to FIG. 3 wherein the mouthpiece or inhalation valve 10 is represented by the rectangle "BREATH IN", which provides a differential pressure on pneumatic lines 12 and 14. The pneumatic lines 12 and 14 are connected to pneumatic inputs 16 and 18, respectively of a transducer 20. The second line can be omitted, and the first used along, developing a pressure differential relative to ambient air pressure. The transducer is of a type having a piezo-electric device therein which produces a signal when a positive pressure is applied to one side, or a negative pressure is applied to the other side. In accordance with the present invention a pressure differential is applied across the piezo-electric device, thus enhancing its response. The transducer is provided with a +5 volt potential at 22 through a type MC78205CP regulator 23 from +8 volts, and is connected to pin 1. The transducer is grounded at 24 on pin 3. A capacitor 25 shunts the voltage at 22 to ground to avoid fluctuations in voltage.

The transducer 20 is of a type which can be purchased for $20, one such transducer being sold by Honeywell under part No. 125PC05D1. This transducer is designed to operate over a range of five pounds per square inch. However, in the present instance a pressure differential of only about 5 centimeters of water is applied, whereby only a small portion of the range of the transducer is used. At its full capacity the transducer will produce an output of 70 millivolts, but due to the small range of the transducer used here only about 400 microvolts is produced from the transducer.

Pins 2 is connected through a resistor 26 to a junction 28 leading to the negative input at pin 6 of an operational amplifier 30. This operational amplifier conveniently is one-half of a package sold by Raytheon as RC4558. Pin 4 of the transducer 20 is connected through a resistor 32 to the positive input at pin 5 of the operational amplifier 30. And this is connected also through a resistor 34 to a 2.5 volt supply. The output of the operation amplifier 30 is taken from pin 7 and leads to a junction 36. The junction is fed back to junction 28 through the parallel combination of a resistor 38 and capacitor 40.

The junction 36 further is connected through a resistor 42 to the negative input at pin 2 of the second operational amplifier 43 of the package, a junction 44 being included on the connecting line. The positive input at pin 3 is connected through a resistor 46 to a positive 2.5 volt supply, and this is shunted by a capacitor 48 connected to ground.

The output of the second operational amplifier 43 is taken from pin 1 and leads to a junction 50. The junction 50 is connected back to junction 44 through the parallel combination of a resistor 52 and a capacitor 54. The output from the junction 50 is connected through the parallel combination of three capacitors 56, 58, and 60 to junctions 62 and 64.

Junction 62 is connected to positive input pin 5 of operational amplifier 66. This again comprises one-half of a dual operational amplifier package which is conveniently a Motorla MC34002BP. The output is taken at pin 7 and leads to a junction 68 having a direct feedback line 70 to a negative input pin 6. This connection is to provide unity gain through the operational amplifier 66.

The output junction 68 is connected to a resistor 74 leading to a junction 76. This junction is connected to a sliding tap 78 on the resistor 74 to vary the effective resistance thereof. The junction further is connected to the negative input pin 2 of the second operational amplifier 80 in the package along with the operational amplifier 66. Positive input pin 3 is connected to junction points 82 and 84 which provide a parallel resistor 86 and capacitor 88 in shunt to ground. Junction point 84 is connected to a resistor 90 leading to the positive 2.5 volt supply. A sliding tap 92 on the resistor 90 is connected back to the line between the resistor and junction point 84 for variation of the resistor to provide an offset adjustment.

The output from the operational amplifier 80 is taken from pin 1 on a line 94, and a parallel resistor 96 and capacitor 98 combination feeds back to the junction 76. The output line continues to pin 2 of a terminal board 100. 2.5 volt potential is supplied to a junction 102 connected through a resistor 104 to the junction 64. The 2.5 volt supply and the junction 102 are also connected to pin No. 11 of a large scale integrated circuit quad CMOS analog switch device 106 sold by Motorola as part No. MC14016BCP. Pin 10 of this device is connected to the junction 64. As will be apparent hereinafter during certain times the pins 10 and 11 are internally short circuited whereby the short circuit the resistor 104.

Pin 14 of the device is provided with a positive 5 volts, while pin 7 is connected to ground. An input is provided to pin 12 from pin 7 of the terminal board 100 across a shunting resistor 110 connected to ground as shown. An appropriate input to pin 12 as supplied from pin 7 of the terminal board causes pins 10 and 11 to short the resistor 104.

The 2.5 volt potential is derived from pin 15 of the terminal board 100 along line 124. 2.5 volts out is indicated by the arrow 122 and is connected to all of the previously mentioned locations supplied with +2.5 volts. This voltage is also connected by a line 126 to pin 1 of the terminal board 100. Pin 12 of the terminal board 100 provides the positive 5 volts, and pins 4 and 14 are grounded. Pin 3 in the present application is not connected.

Figure 4:
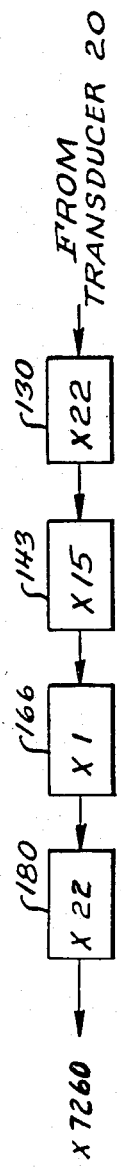
FIG. 4 is a block diagram showing the stages of gain or amplification.

Reference now should be made to FIG. 4 in which the input from the transducer 20 is shown as applied to a "black box" 130 indicated as supplying a multiplying factor of 22. This is in the stage involving the operational amplifier 30. An amplifier stage involving the operational amplifier 43 is indicated by rectangle 143 as having a multiplication factor of 15. Thus, rather high amplification, a factor of 330 is obtained in the first two stages. The third stage indicated at 166 and involving the operational amplifier 66 has a multiplication factor of only 1, this operational amplifier 66 being used primarily as a buffer. The final stage 180 involving the operational amplifier 80 has a multiplication factor of 22, the entire multiplication factor of the several operational amplifiers being 7260.

The operation of the circuit as heretofore described is such that when the person being tested inhales a pneumatic or air pressure differential appears on the one or two pneumatic lines 12 and 14. The transducer produces output voltage having a maximum DC output of about 400 microvolts. This is ultimately amplified to about 3.3 volts without any drift caused by aging of the transducer or otherwise. As will be apparent, with the overall multiplication factor of 7260 a drift of only a half a millivolt could result in an output of zero or nearly five volts for the entire circuit.

As has been noted, the gain is concentrated in the first two amplifier stages, and this is followed by a.c. coupling through the capacitors 56, 58 and 60. The operational amplifier 66 serves as a buffer, and although the gain in the stage involving the operational ampliifer 80 has been indicated as 22, this is adjustable by means of sliding of the tap 78 on the resistor 74. The time constant of the a.c. coupling during breathing, comprising the three capacitors and the resistor 104 is approximately one minute. The output signal from the final operational amplifier 80 is connected to the electronic circuit shown in FIG. 5.

Plus 8 volts is provided on the terminal board 100 on pin 16 thereof, and this leads by way of a line 67 to the top of the operational amplifier 66, the bottom thereof being grounded, as shown.

During inhalation no output is provided from the pin 7 as will be discussed shortly in connection with FIG. 4. However, when there is no breathing, approximately every three seconds there is a short pulse applied from pin 7 to provide an input to pin 12 of the integrated circuit 108, and this causes an internal direct connection or short circuit between pins 10 and 11, thereby shorting out resistor 104, and bringing the output side of the capacitors on junctions 62 and 64 to the +2.5 reference voltage. The switch closure is only on the order of 60 milliseconds. It thus will be seen that any tendency for DC drift of the circuit to the right of the capacitors 56, 58 and 60 is fully compensated by the periodic application of 2.5 volts to the output sides of the capacitors.

It will be apparent that there could be a single capacitor rather than the three shown, but the three are used in parallel in order to obtain the desired capacity at a reasonable cost.

Although appropriate circuit values will no doubt occur to those skilled in the art, representative values which have been found to work are set forth hereinafter by way of example:

Resistor 26=10K OHMS
Resistor 32=10K OHMS
Resistor 34=220K OHMS
Resistor 38=220K OHMS
Resistor 42=10K OHMS
Resistor 46=10K OHMS
Resistor 52=150K OHMS
Resistor 74=20K OHMS
Resistor 86=3.3M OHMS
Resistor 90=20K OHMS
Resistor 96=150K OHMS
Resistor 104=20M OHMS
Resistor 110=180K OHMS
Capacitor 25=0.1 uF
Capacitor 40=1.0 uF
Capacitor 48=2.2 uF
Capacitor 54=1.0 uF
Capacitor 56=1 uF
Capacitor 58=1 uF
Capacitor 60=1 uF
Capacitor 88=2.2 uF
Capacitor 98=1.0 uF The amplified voltage in FIG. 3 is connected to pin 2, the +IN contact of the terminal block 100 which serves as a connector and which could be one-half of a plug and jack for convenience. This amplified voltage is connected to a similar contact on a connector or terminal block 200 forming a part of the adapter shown in FIG. 5. This contact is connected through a wire or other lead 202 to a junction point 204 which continues to one end of a resistor 206, the other end of which is connected to a junction 208. This junction is connected through a resistor 210 to a junction 212, and through a wire 214 to a junction 216. The junction 216 is connected by a wire 218 to a contact labeled as +2.5 on the block of junction 200.

The junction 216 is connected to the top end of cathode 220 of a zener diode 222, the anode of which is grounded. A capacitor 224 is connected in parallel with the zener diode 222, and a resistor 226 is connected to +V. +V is also indicated on the junction or block 200, and is shown as connected through a wire 228 to +5volts. This is derived from the 5 volt voltage supply within the Spirocare apparatus.

As will be understood the resistor 226 serves as a dropping resistor, and the zener diode is one that regulates at 2.5 volts.

The junction 208 is connected to another junction 230 which leads to the + input of an operational amplifier 232. The output is connected to a junction 234 and feeds back to the negative input along a line 236. A +8 volts is connected to the top or No. 8 pin, while the bottom or No. 4 pin is grounded, as shown.

The junction 234 further leads to a resistor 238 connected to a junction 240, the latter being connected to the negative input of an operational amplifier 242. The positive input is connected by means of a sliding tap 244 to a potentiometer resistor 246 having the top end connected to +V i.e., a positive 5 volts and the bottom end connected to ground. The output of the operational amplifier 242 is connected to a junction 248, from which the output signal is fed back to the negative input by means of a parallel resistor 250 and capacitor 252 combination connected to the junction 240.

The junction 248 is connected to a further junction 254 which leads to the No. 5 pin of a voltage controlled oscillator 255, such as an NE555. The No. 1 pin is grounded. +8 volts is connected to the No. 4 pin and to the No. 8 pin, and to one end of a resistor 256 leading to a junction 258 connected to the No. 7 pin. The junction 258 is connected to one end of a resistor 260, the other end of which is connected to a junction 262 leading to the No. 6 pin, and also to a grounded capacitor 264. The output or No. 3 pin is connected to a resistor 266 leading to a junction 268.

The junction 268 leads to a capacitor 270, the opposite side of which is connected to a resistor 272 leading to a junction 274 shunted to ground by a resistor 276. The junction further is connected to the base of an n-p-n transistor 278. The emitter of this transistor is grounded, and the collector is connected to a junction 280, which is in turn connected to a junction 282 leading to a blue coded pin 284 of the plug 21 for connection to the blue coded jack terminal of the Spirocare apparatus.

The junction 280 further is connected through a resistor 286 to a junction 288 leading to a red coded pin 290 of the plug 21 for provision of +5 volts from the Spirocare unit. A +5 volt line 292 leads to a switching converter 296 having a ground connection, and further having a voltage output connection line 308 on which +8 volts is provided by a positive voltage multiplier circuit offered by Intercell in connection with its integrated circuit device ICL7660. In this circuit the ICL7660 chip 298 has pins 3 and 5 grounded. Pin 8 is connected to a junction 294 connected to the +5 volt supply voltage. The junction also is connected to the anode of a diode 300 having the cathode thereof connected to a junction 302. The junction 302 is connected through a capacitor 304 to pin 2 of the chip. The remaining pins, pins 1, 4, 6, and 7 are not connected. The junction 302 further is connected to the anode of a diode 306 having the cathode thereof connected to the +8 volts output line 308, the latter being shunted by a capacitor 310.

In operation of the circuit the pump invertor switches of the ICL7660 chip are used to charge capacitor 304 to a voltage level of $V^+ - V_F$ (where $V^+$ is the supply voltage and $V_F$ is the forward voltage drop of diode 300). On the transfer cycle the voltage on capacitor 304 plus the supply voltage ($V^+$) is applied through diode 306 to capacitor 310. The voltage thus created on capacitor 310 becomes $(2V^+) - (2V_F)$ or twice the supply voltage minus the combined forward voltage drops of diodes 300 and 306. Thus, from an input voltage of 5 volts an output voltage of 8 volts is derived.

The junction 268 is connected to a resistor 312 the opposite side of which is connected to a junction 314. The junction leads to the anode of a diode 316, the cathode of which is connected to the junction 282 previously mentioned. The junction 314 also is connected to a capacitor 318 in series with the resistor 320 leading to a junction 322. The junction 322 is shunted to ground by a resistor 324 and also is connected to the base of an n-p-n transistor 326, the emitter of which is grounded. The collector is connected through a resistor 328 to the positive 5 volt supply line through a line 330, and is also connected through a line 332 to the white coded pin 334 of the plug 21. The fourth pin 336 of the pin is coded black and is grounded, both in the adapter being described and in the Spirocare apparatus.

The junction 230 is connected through a resistor 338 to the anode of a diode 340. The cathode of the diode is connected to a junction 342, which is connected to the junction 212, and which further is connected to the positive input of operational amplifier 346. A line 348 is connected to the junction 204 and to the negative input of the operational amplifier 346. The output of the operational amplifier is connected to a junction 350, and this is connected by a feedback resistor 352 to the negative input line 348. The junction 350 further is connected to a junction 354, which in turn is connected to a resistor 356. The resistor further is connected to a junction 358 having a shunting resistor 359 connected to ground. The junction further is connected to the base of an n-p-n transistor 360. The emitter of this transistor is grounded, and the collector is connected to a junction 362 which leads by way of a line 363 to the junction 268. The transistor 360 operates as an inhibit switch as will be brought out hereinafter.

Junction 254 is connected to the negative input of an operational amplifier 394. The output is connected to a line 396, and this is connected to a feedback resistor 398 to the negative input. The positive input to the 394 operational amplifier comprises the sliding tap 400 on a resistor 402 having the upper end thereof connected to +V and the lower end grounded.

The output line 396 from the operational amplifier 394 is connected to the anode of a diode 404, the cathode of which connects through a line 406 to an audible alarm device 40. The opposite side of the alarm device is connected to the collector of an n-p- transistor 410. The emitter of this transistor is grounded.

The base of the transistor 410 is shunted to ground by a resistor 412, and is connected by another resistor 414 to pin 3 of a ripple counter 415, specifically a type MC14040BCP. Pin 16 of this counter is connected to +V, while pin 8 ($Q_3$) is grounded. Pin 10, which is $\overline{C}$ is connected by a line 416 to the output junction 362 of the inhibit switch transistor 360.

Junction 354 is connected by way of a line 418 to the cathode of a diode 420 paralleling a resistor 422, the anode of the diode 420 and the opposite end of the resistor being connected by a line 424 to the reset pin or terminal of the ripple counter 415, the reset pin being shunted to ground by a capacitor 426.

Output pin 1, $Q_2$, is connected to the anode of a diode 428, the cathode being connected to a junction 430. The junction 430 is connected to the cathode of a diode 432, the anode thereof being grounded. The junction 430 is connected to another junction 434, and a line 436 therefrom leads to terminal SP1 on the terminal board or junction 200, in turn being connected to the like terminal on the terminal board 100 of the amplifier circuit of FIG. 3.

Although the turbine rotor in the mouthpiece of the Spirocare apparatus is intended to rotate in a particular direction upon inhalation, it can also turn in the opposite direction upon exhalation. To prevent false readings, two photoelectric pick-ups are provided in the Spirocare mouthpiece. A hole in the turbine rotor admits light from a source to these two photoelectric or phososensitive pick-ups. Each gives a negative going pulse, and the two pulses must be in the sequence produced by the direction of rotation upon inhalation. A similar result is produced by the present adapter, particularly FIG. 5.

As previously has been noted, an increasing voltage is provided from the throw-away mouthpiece used in the present adapter and the amplifier circuit of FIGS. 2 and 3. The voltage output of the amplifier is applied to pin No. 2, the +IN pin or terminal of the terminal board or connector 100. This voltage then appears as V+ in FIG. 5. The voltage appearing on the line 202 runs from 2.5 volts DC to 5.8 volts DC corresponding to 0 to 4.4 cm. of water. In the Spirocare mouthpiece, the speed of the turbine, and hence the repetition rate of the negative going pulses is directly related to the flow rate through the turbine. The pressure differential in the present mouthpiece is proportional to the square of the velocity. It is necessary to linearize the voltage in order to simulate the frequency produced by the Spirocare unit. This is accomplished by the resistors 206 and 210 in combination with the resistor 338 and the diode 340. For a low pressure voltage range, the resistors 206 and 210, respectively 12K ohms and 33K ohms form a simple voltage divider, providing reduced voltage at the junction 208. As such low voltages the diode 340 does not conduct. Above about 0.6 volts the diode starts to conduct, and the resistor 338, which has a value of 5.1K ohms is placed in parallel with the resistor 210, thus markedly changing the voltage divider. The output voltage at junction 208 and junction 230 versus the input voltage on line 202 changes from a fairly steep slope on the order of 45 degrees, to a relatively shallow slope on the order of perhaps 15 degrees at the 0.6 volts point where the diode starts to conduct. This provides a very close simulation to a square law curve, and linearizes the output voltage relative to the pressure differential produced by the mouthpiece upon inhalation.

The stage including the operational amplifier 232 operates as a 1-to-1 buffer to provide a high impedance, thus avoiding loading of the linearizing network just discussed. Up to this point there is an increase of voltage with an increase of velocity or pressure differential. However, due to the response characteristics of the voltage control oscillator 255 it is desired to have an inverse relation. This is provided by an inverter including the operational amplifier 242 operating with the feedback stage and with the zero set potentiometer 246 and slider 244 to provide an output voltage at the terminals 248 and 254 which varies from 7.0 volts to 2.8 volts DC as the input at the junction 234 varies from 2.5 volts to 3.7 volts DC. The voltage control oscillator, coupled with the external resistor and capacitors produces a series of negative going pulses increasing in frequency with increasing V+, i.e., decreasing voltage into the voltage controlled oscillator. This simulates the output of the turbine of the Spirocare mouthpiece where increased flow (related to pressure or velocity) provides a faster turbine speed.

A pulse from the voltage controlled oscillator and appearing on junction 268 momentarily turns on the transistor 278. This causes a voltage drop across the resistor 286, and delivers a negative going pulse to the blue coded pin 284. The negative going pulse also is connected to the junction 282 and acts through the diode 316 to pull down the junction 314. When the negative pulse heretofore described terminates, the junction 314 returns to a high condition, and renders the transistor 326 conductive until the capacitor 318 charges. This produces a negative going pulse on the while coded terminal 334 delayed in time relative to the negative going pulse on the blue coded terminal 284, but at the same rate. This simulates the succession of pulses produced by the turbine rotor in the Spirocare mouthpiece, and causes the Spirocare apparatus to operate as intended.

The voltage controlled oscillator 255 produces a continuous succession of pulses. It never stops. The turbine rotor of the Spirocare mouthpiece on the other hand produces pulses in the desired sequence only upon inhalation. The adapter circuit of FIG. 5 therefore shunts or inhibits the pulses appearing at the junction 268 by way of the inhibit switch transistor 360 when it is not desired for the adapter to produce the sequence of negative going pulses on the output terminals 284 and 334. To this end the operational amplifier 346 acts as a comparator. An accurate 2.5 volts DC is applied to the positive input thereof from the junction 216 from the zener diode 222, while the Vin+ voltage is applied to the negative terminal and compared therewith. V+ is at 2.5 volts, indicating no pressure differential in the mouthpiece. The transistor 360 is turned on. This effectively shorts the junction 268 to ground, and no output pulses from the voltage controlled oscillator 255 can cause negative going pulses on the output terminals 284 and 334. However, when the Vin+ rises above 2.5 volts, the comparator 346 turns the transistor 360 off, and pulses appearing at 268 pass through the subsequent circuitry to produce the negative going pulses at the output terminals 284 and 334.

As will be recalled from the operation of the amplifier circuit in FIG. 3 the switch 106 is reset every three seconds to reset the capacitors 56, 58 and 60 to prevent drift. Resetting pulses for the switch 106 are provided by the adapter circuit of FIG. 5. A ripple counter 364, specifically a type MC14040BCP, has pin 10, the count pin or C output connected to a junction 366 which leads through a line 368 to a junction 370 on the line between pin 3 of the VCO 255 and the resistor 266. Pin 12 of the ripple counter, the $Q_8$ output, is connected to a junction 372 which leads through a diode 374 to the junction 366. In addition, this junction 372 is connected to a resistor 376 which leads to a junction 378. The junction 378 is connected by means of a resistor 380 to a junction 382 which is grounded through a capacitor 384, and which is also connected to pin 11, the reset pin of the ripple counter. Junction 378 is connected to a junction 386, which is in turn connected through a diode 388 to a junction 390 on the line 418. The junction 386 also is connected by a diode 392 to the junction 434. In each instance it is the anode of the diode that is connected to the junction 386.

The output of the VCO 255 is connected by way of the line 368 and resistor 367 to drive the ripple counter 364. This counter counts up until output $Q_8$ is reached and goes high. This produces a high through the diode 374 to count pin 10 and holds pin 10 high. The counter therefore locks up. The high from $Q_8$ is applied to reset pin 11.

Comparator 346 through line 418, junction 390 and diode 388 holds the junction point 378 low on inhalation. At the end of inhalation, this comparator goes high, and the junction point 378 goes high. The RC network 380, 384 charges and the reset goes high in accordance with the high on the $Q_8$ output. Upon reset, Q8 goes low as does the potential on the junction 378. A pulse thus is produced at the junction, the width of which is determined by the RC time constant of the resistor 380 and capacitor 384.

The time between pulses is determined by the ripple counter as it counts again to $Q_8$ under the control of the VCO 255.

The capacitors 56, 58 and 60 should be reset on ambient pressure. Problems can develop if they are reset on positive pressure. If a connecting tube has a positive pressure entered and is crimped, then reset can take place with positive pressure applied to the transducer 20. The amplifier of FIG. 3 takes this positive pressure as ambient or atmospheric pressure. When the tube is subsequently released and pressure drops to atmospheric pressure, then this would be taken as a negative pressure and a misleading result could be obtained.

Figure 5:
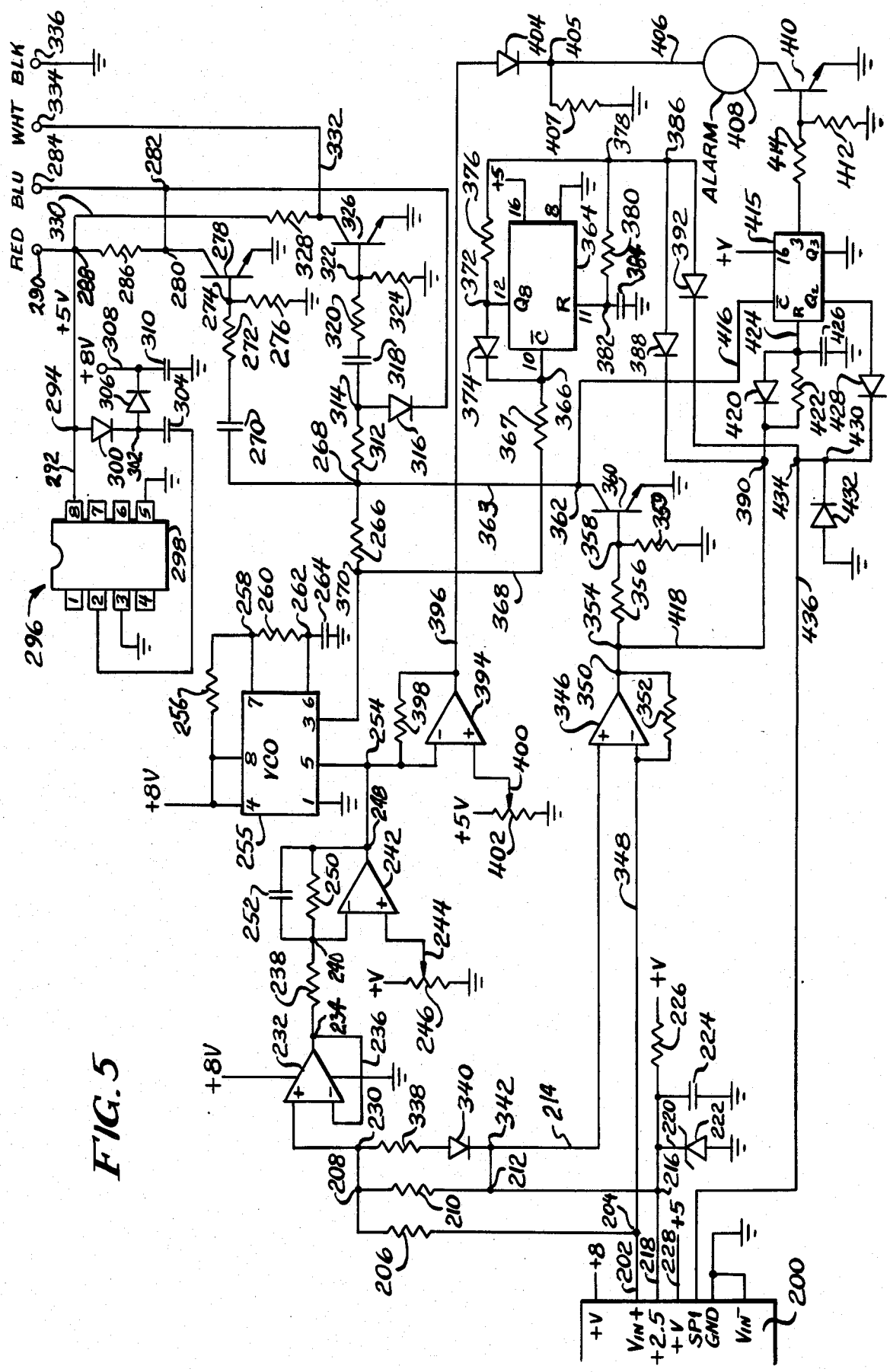
FIG. 5 is an additional electrical circuit diagram showing the adapter for producing output signals identical with those produced by the turbine-type mouthpiece of the Spirocare apparatus.

This is taken care of in the adapter of FIG. 5. The CMOS 12 bit ripple counter 415 receives the inputs of line 416 from the voltage controlled oscillator 255. It gets count pulses the same as the output terminals 284 and 334 and when it reaches a total count equal to 5.5 liters of inhaled air or oxygen, the highest possible reading, the counter recognizes this or anything above it as being too high a reading and provides a fault output through the diode 428 to the line 436 to SP1. This is a steady state output of a flip-flop. The reset input to this counter is tied to the output of the comparator 346 that controls the inhibit switch transistor 360. If the comparator output is high it resets the counter and terminates the high output therefrom. The resistor 422 is of a 1 Megohm value, the the capacitor 426 is one microfarrad, giving a delay to insure that the analog circuit is solidly reset. The diode 420 in parallel with the resistor 422 affords a rapid discharge of the capacitor. It is possible that a single time lapse pulse might not reset the counter if a hard fault condition existed. Accordingly, there is provided a cause and effect situation in that the output of the comparator which is controlled by the output of the amplifier circuit of FIG. 3 causes a reset of the counter 415, and the termination of the high output of the counter is brought about by the reset.

One other function of the adapter circuit of FIG. 5 remains. If a patient should breathe too fast provision is made for sounding an alarm. As long as the output at junction 248 is at or above 2.8 volts all is well. However, if the patient breathes too rapidly and produces too high a volume flow, then the voltage drops below 2.8 volts, and there is a high outut from the comparator 394. This high output is applied to the like 396 and through the diode 404 and the line 406 to the alarm sound device 408. The line 406 has a junction 405 to which is connected a shunt resistor 407 to ground. The transistor 410 turns off and on under the control of the ripple counter 415 so that a discontinuous sound in the nature of chirping is produced by the alarm 408.

The turbine pick-up of the Spirocare unit including the photosensitive devices and the accompanying electronic circuitry require approximately 35 to 40 milliamps at 5 volts. The Spirocare apparatus provides 5 volts on the red coded socket connection cooperable with the terminal 290, and has a significant safety margin in providing the 35–40 ma. current. In an actual amplifier and adapter circuit constructed in accordance with FIGS. 3 and 5 it has been found that about 20 ma. at 5 volts is required, plus approximately 12 ma. at 5 volts to operate the switching converter 296 to provide the 8 volt output thereof, thus requiring a total of 32 ma. well below the requirements of the Spirocare mouthpiece.

The entire circuitry of FIGS. 3 and 5 is incorporated in the rectangular housing 19 which fits readily within the cavity 17 in the Spirocare apparatus 11, the four pin plug 21 on the housing 19 plugging into the Spirocare apparatus socket upon insertion of the housing into the cavity. The Spirocare apparatus then works quite well with the aforesaid adaptive circuitry and the pressure differential mouthpiece, which is of plastic and elastomeric construction and sufficiently inexpensive is to be thrown away after use by a single patient. There are thus no problems of sterilzation of a mouthpiece, no problems of a psychological nature through a patient's knowing that he may be using a previously used mouthpiece, albeit sterilized, and no problems of financial expense since the mouthpiece is quite inexpensive and can be thrown away if dropped. The original equipment Spirocare mouthpiece including the electronics is not well adapted to sterilization, is too expensive for throw away use, and is expensive to repair if dropped on a hard floor.

Specific circuit valves will probably occur to those skilled in the art, and representative values used in an actual circuit are as follows:

Resistor 210=33K OHMS
Resistor 226=22K OHMS
Resistor 238=10K OHMS
Resistor 246=20K OHMS
Resistor 250=33K OHMS
Resistor 256=47K OHMS
Resistor 260=47K OHMS
Resistor 266=6.8K OHMS
Resistor 272=10K OHMS
Resistor 276=100K OHMS
Resistor 286=2.2K OHMS
Resistor 312=10K OHMS
Resistor 320=10K OHMS
Resistor 324=100K OHMS
Resistor 328=2.2K OHMS
Resistor 338=5.1K OHMS
Resistor 352=100K OHMS
Resistor 356=10K OHMS
Resistor 359=3.3K OHMS
Resistor 367=22K OHMS
Resistor 372=100K OHMS
Resistor 376=10K OHMS
Resistor 380=150K OHMS
Resistor 388=1M OHMS
Resistor 390=1M OHMS
Resistor 398=100K OHMS
Resistor 402=20K OHMS
Resistor 407=22K OHMS
Resistor 412=47K OHMS
Resistor 414=10K OHMS
Resistor 422=1M OHMS
Capacitor 224=1 uF
Capacitor 252=1 uF
Capacitor 264=0.05 uF
Capacitor 270=0.01 uF
Capacitor 304=10 uF
Capacitor 310=10 uF
Capacitor 318=0.01 uF
Capacitor 384=0.47 uF
Capacitor 392=1 uF
Capacitor 426=1 uF The specific examples of the invention as shown and described herein are for illustrative purposes only. Various changes in structure will no doubt occur to those skilled in the art, and will be understood as forming a part Of the present invention insofar as they fall within the spirit and scope of the appended claims.

The invention is claimed as follows:

1. Adapter for use with inhalation therapy apparatus for detecting patient inhalation and of a type normally having a turbine type mouthpiece and receiving a series of sequential pairs of electric pulses from said mouthpiece, said adapter comprising a replacement mouthpiece for said turbine type mouthpiece and having fixed flow restricting means for developing a pressure differential upon patient inhalation, a housing remote relative to said replacement mouthpiece, solid state air pressure-to-electric voltage transducer means in said housing, pneumatic tubing means connecting said pressure differential means and said transducer means for converting said pressure differential into a voltage proportional to said pressure differential, electric circuit means in said housing interconnected with said transducer means for producing a series of pairs of pulses related to said voltage, inhalation through said replacement mouthpiece producing said pairs of pulses in a desired predetermined sequence and at a repetition rate proportional to the volumetric rate of patient inhalation, and means for electrically connecting the pulses so produced by said pulse producing means to said apparatus to operate said apparatus.

2. An adapter as set forth in claim 1 wherein the pulse producing means comprises two pulse producing means, and means interconnecting said pulse producing means whereby one thereof controls the other to provide a predetermined sequence to said pairs of pulses.

3. An adapter as set forth in claim 2 and further including pulse inhibiting means connected with said pulse producing means and with said transducer means to inhibit production of pulses except during patent inhalation.

4. An adapter as set forth in claim 1 wherein said pulse producing means comprises a voltage controlled oscillator, and two interconnected pulse producers connected to said voltage controlled oscillator, one of said pulse producers controlling the other to insure a predetermined sequence of said pairs of pulses.

5. An adapter as set forth in claim 1 and further including pulse inhibiting means connected with said pulse producing means and with said transducer means to inhibit production of pulses except during patient inhalation.

6. An adapter as set forth in claim 1 and further including between said transducer means and said pulse producing means voltage inversion means for causing voltage applied to said pulse producing means to have an inverse relation to the pressure differential developed by said mouthpiece.

7. An adapter as set forth in claim 6 wherein said pulse producing means comprises a voltage controlled oscillator, and two interconnected pulse producers connected to said voltage controlled oscillator, one of said pulse producers controlling the other to insure a predetermined sequence of said pairs of pulses.

8. An adapter as set forth in claim 7 and further including pulse inhibiting means connected with said pulse producing means and with said transducer means to inhibit production of pulses except during patient inhalation.

9. An adapter as set forth in claim 1 wherein said transducer means includes at least two stages of amplification coupled through a capacitor, a switch interconnected with said capacitor and periodically operated to reset said capacitor to prevent amplifier drift, and means interconnected with said pulse producing means and with said switch to generate a series of reset pulses to operate said switch.

10. An adapter as set forth in claim 9 and further including means interconnected with said reset pulse generating means to inhibit reset pulses during patient inhalation.

11. An adapter as set forth in claim 1 and further including alarm means interconnected with said pulse producing means to produce an alarm if the voltage supplied to said pulse producing means from said transducer means is outside a predetermined range.

12. An adapter as set forth in claim 1 and further including inhalation therapy apparatus having a cavity therein for storage of said turbine type mouthpiece and including an electrical connector for said mouthpiece in said cavity, and said housing for said transducer means and said pulse producing means is mountable within said cavity and has an electrical connector engageable with the electrical connector in said cavity.

* * * * *